US011738506B2

(12) United States Patent
You (10) Patent No.: US 11,738,506 B2
(45) Date of Patent: Aug. 29, 2023

(54) 3D BIOPRINTER

(71) Applicant: ROKIT HEALTHCARE INC., Seoul (KR)

(72) Inventor: Seok Hwan You, Seoul (KR)

(73) Assignee: ROKIT HEALTHCARE INC., Seoul (KR)

( * ) Notice: Subject to any disclaimer, the term of this patent is extended or adjusted under 35 U.S.C. 154(b) by 453 days.

(21) Appl. No.: 16/342,780

(22) PCT Filed: Oct. 18, 2017

(86) PCT No.: PCT/KR2017/011527
§ 371 (c)(1),
(2) Date: Apr. 17, 2019

(87) PCT Pub. No.: WO2018/074838
PCT Pub. Date: Apr. 26, 2018

(65) Prior Publication Data
US 2019/0232558 A1   Aug. 1, 2019

(30) Foreign Application Priority Data

Oct. 19, 2016  (KR) ........................ 10-2016-0135665

(51) Int. Cl.
*B29C 64/165* (2017.01)
*B29C 31/04* (2006.01)
(Continued)

(52) U.S. Cl.
CPC ............ *B29C 64/165* (2017.08); *B29C 31/04* (2013.01); *B29C 31/10* (2013.01); *B29C 64/106* (2017.08);
(Continued)

(58) Field of Classification Search
CPC ..... B29C 64/165; B29C 64/20; B29C 64/209; B29C 64/245; B29C 64/295
See application file for complete search history.

(56) References Cited

U.S. PATENT DOCUMENTS 4,619,316 A * 10/1986 Nakayama ............ F28F 13/187
                                                          165/104.33
5,572,431 A * 11/1996 Brown ................ B29C 67/0048
                                                                700/95
(Continued)

FOREIGN PATENT DOCUMENTS

CN     105652922 A    6/2016
JP     H0534184 A     2/1993
(Continued)

OTHER PUBLICATIONS

International Search Report issued in corresponding International Application No. PCT/KR2017/011527 dated Jan. 19, 2018 (2 pages).
(Continued)

*Primary Examiner* — Yunju Kim
(74) *Attorney, Agent, or Firm* — Osha Bergman Watanabe & Burton LLP (57) ABSTRACT

The present invention relates to a 3D bioprinter. The 3D bioprinter, according to the present invention, comprises: a case inside of which a work space is provided; a printing plate installed inside of the case so as slide in the forward, backward, left, and right directions; a first nozzle installed inside the case for dispensing a biomaterial in a solid state on the printing plate; a second nozzle installed inside the case for dispensing a biomaterial in a liquid state on the printing plate; and a control unit for controlling the dispensing by the first nozzle and the second nozzle, wherein the first nozzle and the second nozzle are used to print a single
(Continued)

structure by stacking the biomaterial in the solid state and the biomaterial in the liquid state.

6 Claims, 5 Drawing Sheets

(51) Int. Cl.
| | |
|---|---|
| *B29C 31/10* | (2006.01) |
| *B29C 64/106* | (2017.01) |
| *B29C 64/20* | (2017.01) |
| *B29C 64/209* | (2017.01) |
| *B29C 64/25* | (2017.01) |
| *B29C 64/295* | (2017.01) |
| *B29C 64/364* | (2017.01) |
| *B29C 64/386* | (2017.01) |
| *B29C 64/393* | (2017.01) |
| *B29C 67/00* | (2017.01) |
| *B33Y 40/00* | (2020.01) |
| *B33Y 70/00* | (2020.01) |
| *C12M 3/00* | (2006.01) |
| *B33Y 30/00* | (2015.01) |
| *B33Y 50/02* | (2015.01) |
| *C12N 5/00* | (2006.01) |

(52) U.S. Cl.
CPC ............ *B29C 64/20* (2017.08); *B29C 64/209* (2017.08); *B29C 64/25* (2017.08); *B29C 64/295* (2017.08); *B29C 64/364* (2017.08); *B29C 64/386* (2017.08); *B29C 64/393* (2017.08); *B29C 67/00* (2013.01); *B33Y 40/00* (2014.12); *B33Y 70/00* (2014.12); *C12M 21/08* (2013.01); *B33Y 30/00* (2014.12); *B33Y 50/02* (2014.12); *C12N 5/0062* (2013.01); *C12N 2513/00* (2013.01)

(56) References Cited

U.S. PATENT DOCUMENTS

| | | | |
|---|---|---|---|
| 10,336,056 B2 * | 7/2019 | Hemphill | B29C 64/106 |
| 2015/0072293 A1 * | 3/2015 | DeSimone | B29C 64/245 |
| | | | 430/322 |
| 2015/0128528 A1 * | 5/2015 | Lacaze | B29C 64/371 |
| | | | 53/431 |
| 2015/0174824 A1 | 6/2015 | Gifford et al. | |
| 2016/0200024 A1 * | 7/2016 | Kim | B29C 48/832 |
| | | | 425/375 |
| 2017/0136700 A1 * | 5/2017 | Li | B29C 64/112 |
| 2018/0104864 A1 * | 4/2018 | Balka | B29C 33/04 |
| 2018/0326665 A1 * | 11/2018 | Gatenholm | B01L 1/02 |

FOREIGN PATENT DOCUMENTS

| | | | |
|---|---|---|---|
| JP | 2003011237 A | 1/2003 | |
| JP | 2015112751 A | 6/2015 | |
| JP | 2015205455 A | 11/2015 | |
| JP | 2016144868 A | 8/2016 | |
| KR | 10-2011-0071985 A | 6/2011 | |
| KR | 10-2013-0005768 A | 1/2013 | |
| KR | 10-2016-0023874 A | 3/2016 | |
| KR | 10-2016-0096829 A | 8/2016 | |
| KR | 10-2016-0112797 A | 9/2016 | |
| WO | 2015060923 A1 | 4/2015 | |

OTHER PUBLICATIONS

Written Opinion issued in corresponding International Application No. PCT/KR2017/011527 dated Jan. 19, 2018 (5 pages).
Office Action issued in corresponding European Application No. 17862028.2, dated Apr. 24, 2020 (7 pages).
Second Office Action issued in corresponding Chinese Application No. 201780064263.0 dated May 24, 2021 (18 pages).
Office Action issued in corresponding JP Application No. 2019-520747 with English translation dated Sep. 14, 2021 (13 pages).

* cited by examiner

3D BIOPRINTER

TECHNICAL FIELD

The present invention relates to a three-dimensional (3D) bioprinter, and more specifically, to a 3D bioprinter capable of printing in one structure by stacking a solid state biomaterial and a liquid state biomaterial.

BACKGROUND ART

Recently, since demands in a research field of tissue engineering and regenerative medicine and a customized medical service are increasing, research for a 3D printer using a biomaterial is actively proceeding.

The 3D printer includes a frame which configures xzy axes and a nozzle having a dispenser shape to discharge the biomaterial. The conventional 3D printer fills a fluid state biomaterial having viscosity such as collagen, gelatin, or the like in the nozzle. A method of pushing and discharging the biomaterial by connecting a pneumatic system to the nozzle in which the fluid state biomaterial is filled is in use.

However, in the discharging method like the above, when a biomaterial is not in a fluid state (for example, when a biomaterial is in a solid state such as a powder, a pallet grain, or the like), the nozzle should be heated to a high temperature to discharge the biomaterial after converting the biomaterial to the fluid state. Accordingly, in order to use a fluid biomaterial and a solid biomaterial together, since a process of cooling the nozzle after heating the nozzle is repeated, a problem can occur due to overload of the nozzle.

Further, a biomaterial which is sensitive to a temperature environment should be hardened by a predetermined time interval after being discharged but is hardened directly after being discharged due to an unsuitable temperature environment.

DISCLOSURE

Technical Problem

The present invention is directed to providing a 3D bioprinter capable of printing in one structure using a fluid state biomaterial and a solid state biomaterial together.

Further, the present invention is directed to providing a 3D bioprinter capable of adjusting a temperature of each of a nozzle configured to discharge a biomaterial and a printing plate on which a structure is stacked.

Purposes of the present invention are not limited to the above and other unmentioned purposes may be apparent to those skilled in the art from the following description.

Technical Solution

The present invention provides a 3D bioprinter.

According to one embodiment of the present invention, the 3D bioprinter includes: a case in which a working space is provided; a printing plate installed in the case and configured to slidingly move in vertical and lateral directions; a first nozzle installed in the case and configured to discharge a solid state biomaterial to the printing plate; a second nozzle installed in the case and configured to discharge a fluid state biomaterial to the printing plate; and a controller configured to control discharge of the first nozzle and the second nozzle, wherein the first nozzle and the second nozzle are used to stack the solid state biomaterial and the fluid state biomaterial to be printed in one structure.

According to one embodiment, the 3D bioprinter may further include a temperature adjusting part connected to the case to adjust a temperature of at least one of the printing plate and the second nozzle, wherein the controller may control the temperature adjusting part.

According to one embodiment, the controller may be provided to independently control the temperature of each of the printing plate and the second nozzle through the temperature adjusting part.

According to one embodiment, the controller may be provided to independently control the first nozzle and the second nozzle.

According to one embodiment, the controller may control the second nozzle to gradationally discharge the fluid state biomaterial and the gradational discharge may be performed by a step motor connected to the second nozzle.

According to one embodiment, the 3D bioprinter may further include an insulation cover configured to surround an exterior of the second nozzle and insulate the second nozzle.

According to one embodiment, the temperature adjusting part may include a water tank configured to store cooling water; a Peltier member in which, when a temperature of one surface rises, a temperature of the other surface falls; and a heating member configured to increase the temperature of each of the printing plate and the second nozzle.

According to one embodiment, the temperature adjusting part may include a transferring member configured to allow the cooling water to come into contact with the Peltier member and a pump configured to transfer the cooling water, and the Peltier member may be attached to each of the printing plate and the second nozzle to decrease the temperature of each of the printing plate and the second nozzle.

According to one embodiment, the case may be provided with a door configured to open or seal the working space.

According to one embodiment, a purifying member configured to purify the working space may be provided in the case.

Advantageous Effects

According to one embodiment of the present invention, a fluid state biomaterial and a solid state biomaterial can be used together to be printed in one structure.

Further, a structure, of which the outside is in a solid state and the inside is in a fluid state, can be manufactured by adjusting a temperature of each of a nozzle configured to discharge the biomaterial and a printing plate on which the structure is stacked.

Effects of the present invention are not limited to the above-described effects and unmentioned effects may be apparent to those skilled in the art from the specification and the accompanying drawings.

MODES OF THE INVENTION

Hereinafter, embodiments of the present invention will be described in more detail with reference to the accompanying drawings. The embodiments of the present invention may be transformed to various shapes, so a scope of the present invention should not be limited to the following embodiments. The embodiments are provided to more completely describe the present invention to those skilled in the art. Accordingly, shapes of elements in the drawings are exaggerated for more apparent descriptions.

Hereinafter, an example of the present invention will be described in detail with reference to FIGS. 1 to 6.

Figure 1:
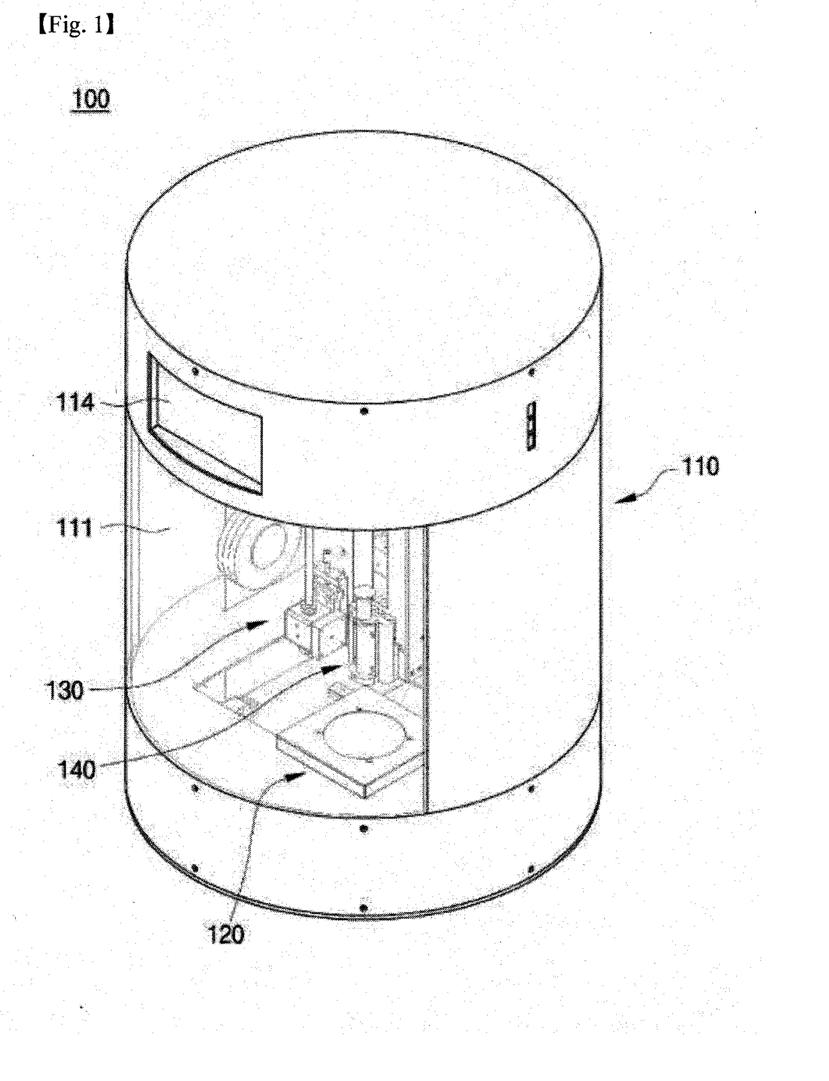
FIG. 1 is a perspective view illustrating a 3D bioprinter according to the present invention.
Figure 2:
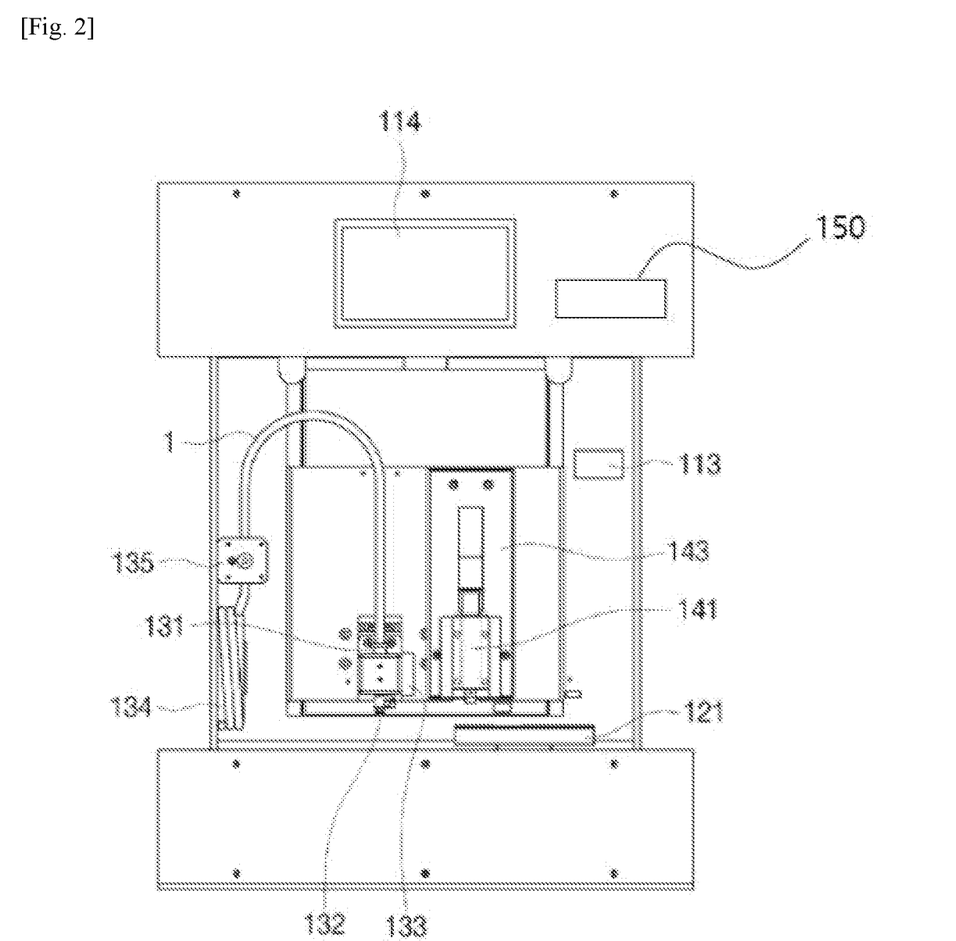
FIG. 2 is a front view illustrating the 3D bioprinter according to the present invention.

FIG. 1 is a front view illustrating a 3D bioprinter 100 according to the present invention, and FIG. 2 is a front view illustrating the 3D bioprinter 100 according to the present invention. Referring to FIGS. 1 and 2, the 3D bioprinter 100 according to the present invention includes a case 110, a stage unit 120, a first nozzle 130, a second nozzle 140, a controller 150, and a temperature adjusting part 160.

The case 110 may be provided in a cylindrical shape having a working space therein. The case 110 may be provided with a door 111 configured to open or seal the working space. The working space may be provided with a thermometer 113 on which a temperature in the case 110 is displayed.

Figure 4:
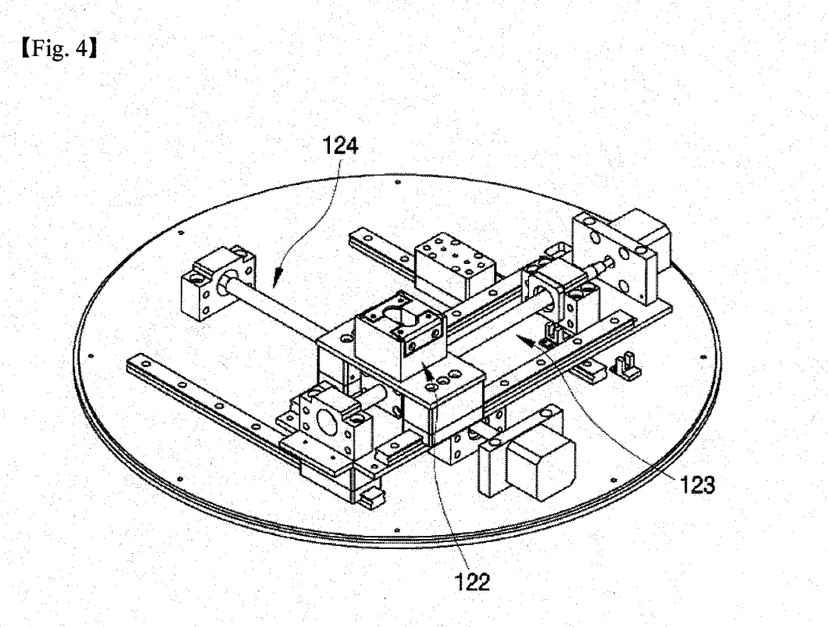
FIG. 4 is a perspective view illustrating a moving structure of a stage unit shown in FIG. 1.

The stage unit 120 is provided to be slidable in vertical and lateral directions. FIG. 4 is a perspective view illustrating a moving structure of the stage unit 120 shown in FIG. 1. Referring to FIG. 4, the stage unit 120 includes a printing plate 121, a coupling member 122, a front and rear guide member 123, and a right and left guide member 124. The coupling member 122 is located under the case 110 and fix-coupled to the printing plate 121. The front and rear guide member 123 is provided to be connected to the coupling member 122 so that the printing plate 121 may slide in frontward and backward directions. The right and left guide member 124 is provided to be connected to the front and rear guide member 123 so that the printing plate 121 may slide in rightward and leftward directions.

The first nozzle 130 discharges a solid state biomaterial 1 to the printing plate 121. The solid state biomaterial 1 may be a polymer biomaterial in a filament (a wire having a cross-sectional surface in a circular shape) type. The first nozzle 130 is installed in the working space in the case 110.

Figure 3:
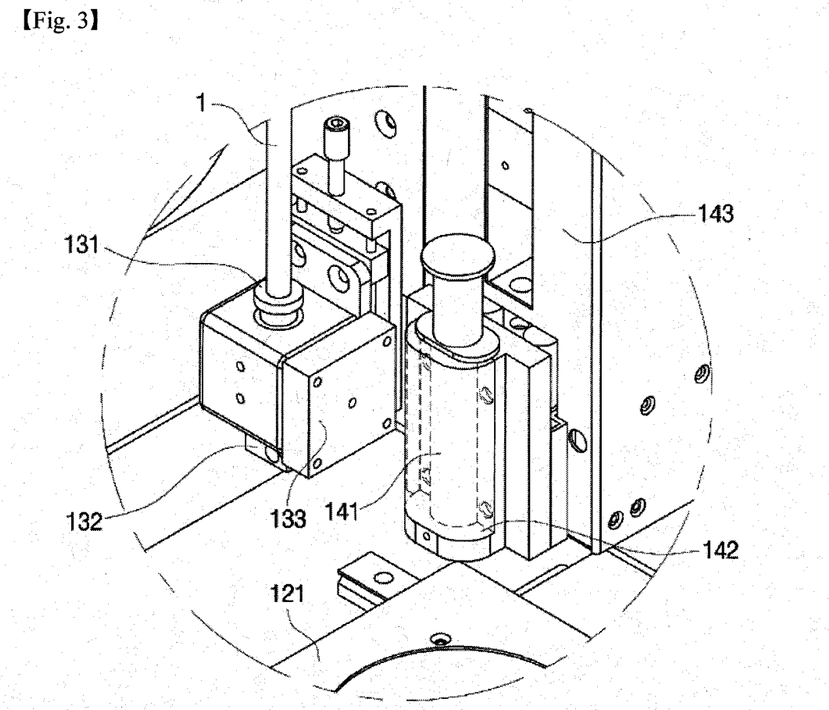
FIG. 3 is a perspective view illustrating a first nozzle and a second nozzle shown in FIG. 1.

FIG. 3 is a perspective view illustrating the first nozzle 130 and the second nozzle 140 shown in FIG. 1. Referring to FIG. 3, the first nozzle 130 includes an introduction port 131 and a discharge port 132. The introduction port 131 is provided at an upper portion of the first nozzle 130 and the solid biomaterial 1 is introduced through the introduction port 131. The discharge port 132 extrudes and discharges the solid biomaterial 1 introduced through the introduction port 131. A fan 133 may be provided at one side of the first nozzle 130 to prevent overload when the first nozzle 130 is extruded.

As shown in FIG. 2, the solid biomaterial 1 discharged through the first nozzle 130 is usually wound around a winding member 134 provided at one side of the working space to be stored in the working space, and passes through the guide member 135 to prevent separation of the solid biomaterial 1 and then is introduced into the introduction port 131 when used.

The first nozzle 130 may be provided as an extruder nozzle. As an example, a size of a discharge port of the extruder nozzle may be provided to be 0.2 to 0.4 mm. A thermoplastic resin extrusion lamination method (fused filament fabrication) may be used as an extruding method of the first nozzle 130.

The second nozzle 140 discharges a fluid state biomaterial to the printing plate 121. The second nozzle 140 may be provided as a dispenser nozzle.

The second nozzle 140 is installed in the working space in the case 110. Referring to FIG. 3, the second nozzle 140 includes a housing 141, an insulation cover 142, and a step motor 143. The fluid state biomaterial is stored in the housing 141. The housing 141 may be provided in a syringe form.

The insulation cover 142 surrounds the outside of the housing 141 and insulates the fluid state biomaterial which is sensitive to temperature variation from the outside.

The step motor 143 pushes the housing 141 in a downward direction according to an electric signal to discharge the fluid state biomaterial. The step motor 143 may move by 1.5 microns as a resolution (a moving distance by a minimal electric signal). Accordingly, the fluid state biomaterial may be gradationally discharged by 1.5 microns. As an example, a size of a discharge port of the dispenser nozzle may be provided to be 0.05 to 0.8 mm. Accordingly, a fluid biomaterial in a gel shape such as a hydrogel or the like may be discharged by 1.5 microns.

A light source module may be installed under the second nozzle 140. The light source module may generate an ultraviolet wavelength to harden a photocurable fluid state biomaterial. As an example, when the photocurable fluid state biomaterial is discharged from the second nozzle 140, the fluid state biomaterial may be hardened using the light source module directly when discharged. Accordingly, the light source module may prevent collapse of the discharged fluid state biomaterial.

The controller 150 controls discharge of the first nozzle 130 and second nozzle 140. As an example, the first nozzle 130 discharges so that the outside of a structure becomes a hard tissue, and the second nozzle 140 fills the inside of the structure using the liquid state biomaterial. Accordingly, the structure may be stacked in a core-shell structure. That is, the solid state biomaterial and the liquid state biomaterial may be used together to be combined and stacked as one structure. The controller 150 controls the temperature adjusting part 160 which will be described below.

Figure 5:
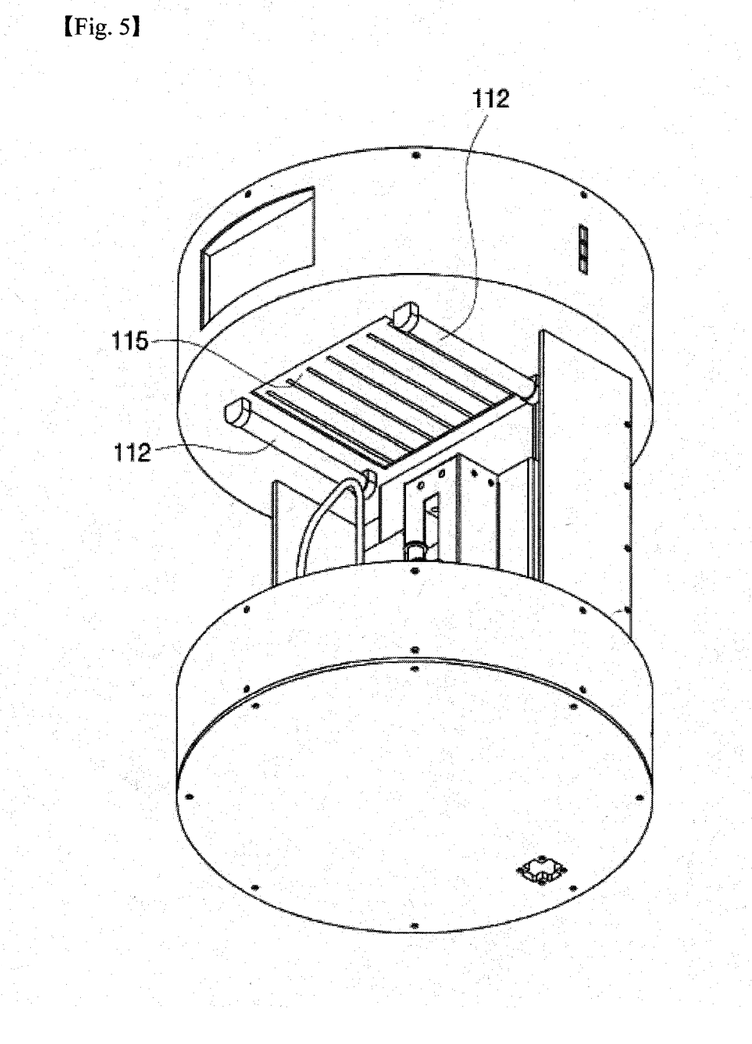
FIG. 5 is a perspective view illustrating a purifying member and a ventilation member according to an embodiment of the present invention.

FIG. 5 is a perspective view illustrating a purifying member 112 and a ventilation member 115 according to the embodiment of the present invention. Referring to FIG. 5, at least one sterilizing purifying member 112 may be installed on the working space of the case 110. Further, the ventilation member 115 configured to circulate air in the working space may be installed on the working space of the case 110. The purifying member 112 may be provided as a sterilizing UV lamp. A plurality of purifying members 112 may be installed on the working space. The purifying member 112 sterilizes deleterious microorganisms or the like in the working space. The ventilation member 115 is provided to maintain cleanliness of air introduced into the working space and prevent discharge of the deleterious microorganisms from the working space to the outside. The ventilation member 115 may be provided as a high efficiency particulate air (HEPA) filter.

Figure 6:
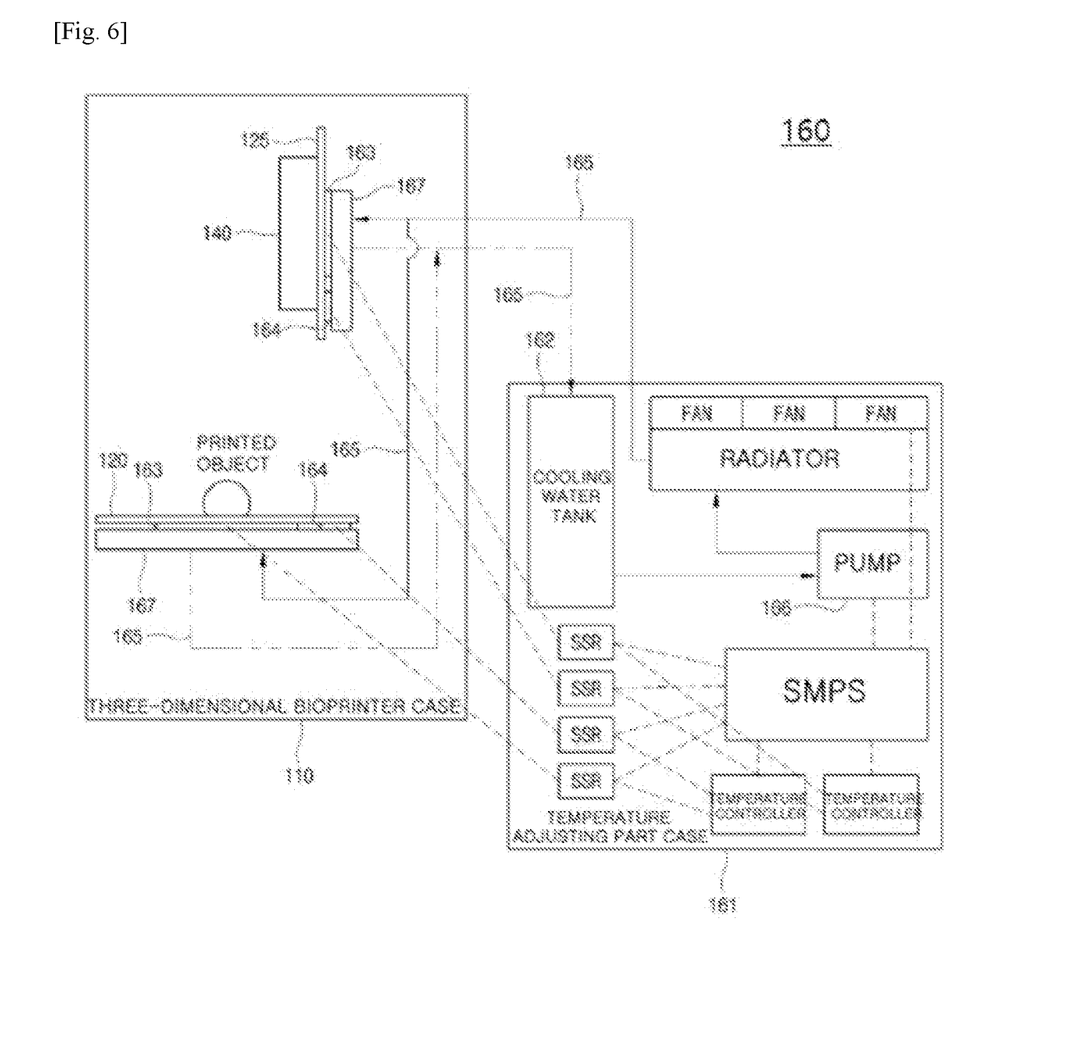
FIG. 6 is a view illustrating a temperature adjusting part according to the embodiment of the present invention.

FIG. 6 is a view illustrating the temperature adjusting part 160 according to the embodiment of the present invention. Referring to FIG. 6, the temperature adjusting part 160 includes a temperature adjusting part case 161, a water tank 162, Peltier members 163, heating members 164, and heat conductive plates 167. The temperature adjusting part 160 is connected to the case 110 to adjust a temperature of at least one of the printing plate 121 and the second nozzle 140. The temperature adjusting part 160 is controlled by the controller 150.

The temperature adjusting part case 161 provides an inner space. The temperature adjusting part case 161 may be formed of a metal material and, as an example, may be formed of aluminum.

The water tank 162 may store cooling water. The water tank 162 is provided in the temperature adjusting part case 161.

The Peltier member 163 may decrease the temperature of each of the printing plate 121 and the second nozzle 140. As an example, the Peltier member 163 may decrease the temperature of each of the printing plate 121 and the second nozzle 140 to −10° C. using the controller 150. In the Peltier member 163, when power is supplied from a power supply device (SMPS) and thus a temperature of one surface rises, a temperature of the other surface falls. The Peltier member 163 is attached to one side of each of the printing plate 121 and the second nozzle 140. Cross-sectional surfaces of the Peltier member 163 which come into contact with the printing plate 121 and the second nozzle 140 are different surfaces.

The heating member 164 is attached to one side of the printing plate 121. Further, the heating member 164 is attached to one side of the second nozzle 140. As described above, the heating member 164 may be provided as a pair. The heating member 164 may receive the power from the power supply device (SMPS) to increase the temperature of each of the printing plate 121 and the second nozzle 140. As an example, the heating member 164 may increase the temperature of each of the printing plate 121 and the second nozzle 140 to 80° C. using the controller 150.

The heat conductive plates 167 are attached to the Peltier members 163 and the heating members 164. The heat conductive plates 167 transfer thermal energy generated from the Peltier members 163 and the heating members 164 to the printing plate 121 and the second nozzle 140. The heat conductive plate 167 may have a large area which comes into contact with the printing plate 121 and the second nozzle 140 to improve a heat transfer rate.

The temperature adjusting part 160 includes a transferring member 165, a pump 166, and a radiator.

The transferring member 165 may transfer the cooling water to the Peltier members 163 and the heating members 164. In this case, the pump 166 and the radiator may adjust the speed of the cooling water which is transferred.

A heat conductive fixing member 125 may be provided between the second nozzle 140 and the Peltier member 163. The heat conductive fixing member 125 may fix the second nozzle 140 to one side of the case 110. The heat conductive fixing member 125 may transfer thermal energy transferred from the temperature adjusting part 160 to the second nozzle 140.

Hereinafter, a method of stacking the fluid state biomaterial in a 3D structure using the 3D bioprinter 100 will be described.

A biomaterial "A" is configured to maintain a fluid state at room temperature and is hardened only in a predetermined temperature range. In order to stack the 3D structure using the biomaterial "A", the temperature of the second nozzle 140 into which the biomaterial "A" is injected is maintained at room temperature using the temperature adjusting part 160. The temperature of the printing plate 121 is maintained at a particular temperature using the temperature adjusting part 160. The biomaterial "A" injected into the second nozzle 140 is discharged to the printing plate 121 in the predetermined temperature range. The fluid state biomaterial "A" is hardened on the printing plate 121 while being discharging and thus may be stacked in the 3D structure. As described above, a biomaterial hardened or fluidized in a set temperature range may be stacked in a 3D structure.

As described above, since the printing plate 121 and the second nozzle 140 of which the temperatures may be adjusted are used, various biomaterials hardened or fluidized in a set temperature range may be used as a material of a 3D structure.

For convenience of users, a function for adjusting the temperatures of the printing plate 121 and the second nozzle 140 may set a temperature through a touch screen 114 provided on the case 110. Further, remote control may be performed due to connection between an android-based mobile terminal and the 3D bioprinter 100.

The above detailed description is provided to exemplify the present invention. Further, the above description shows and describes the embodiment of the present invention and may be used in various different combinations, changes, and environments. That is, changes and modifications may be performed in a scope of a concept of the present invention disclosed in the specification, an equivalent of the above disclosure, and/or scope of a technology or knowledge in a corresponding field. The above-described embodiment is provided to an optimum state for implementing technical spirit of the present invention, and various modifications required in specific application fields and usages in the present invention. Accordingly, the detailed description in the present invention does not limit the present invention from the disclosed embodiment. Further, appended claims include other embodiments.

REFERENCE NUMERALS

1: solid biomaterial
100: 3D bioprinter
110: case
111: door
112: purifying member
113: thermometer
114: touch screen
115: ventilation member
120: stage unit
121: printing plate
122: coupling member
123: front and rear guide member
124: right and left guide member
125: heat conductive fixing member
130: first nozzle
131: introduction port
132: discharge port
133: fan
134: winding member
135: guide member
140: second nozzle
141: housing
142: insulation cover
143: step motor
150: controller
160: temperature adjusting part
161: temperature adjusting part case
162: water tank
163: Peltier member 164: heating member
165: transferring member
166: pump
167: heat conductive plate

The invention claimed is:

1. A three-dimensional (3D) bioprinter comprising:
a case provided with a door configured to open and close a working space to separate the working space from an outside;
a stage unit provided with a printing plate installed in the working space and configured to move in front-rear and left-right directions;
a first nozzle installed in the working space and configured to discharge a solid state biomaterial to the printing plate;
a second nozzle installed in the working space and configured to discharge a fluid state biomaterial to the printing plate, wherein the second nozzle includes a housing in which the fluid state biomaterial is stored;
a temperature adjusting part connected to the case to adjust a temperature of the printing plate and the second nozzle; and
a controller configured to control discharge of the first nozzle and the second nozzle,
wherein the controller controls the first nozzle and the second nozzle to stack the solid state biomaterial and the fluid state biomaterial to be printed in one structure, and wherein the first nozzle discharges so that the structure becomes a hard tissue using the solid state biomaterial, and the second nozzle fills the inside of the structure using the liquid state biomaterial,
wherein the temperature adjusting part includes:
a plurality of Peltier members disposed in the working space and configured to reduce the temperature of the second nozzle and the printing plate, the plurality of Peltier members including a first Peltier member installed on the side of the second nozzle and a second Peltier member installed on the side of the printing plate;
a plurality of heating members disposed in the working space and configured to increase the temperature of each of the printing plate and the second nozzle, the plurality of heating members including a first heating member installed on the side of the second nozzle, and a second heating member installed on the side of the printing plate;
a temperature adjusting part case spaced apart from the working space;
a water tank disposed in the temperature adjusting part case and configured to store cooling water;
a plurality of transferring members for transferring the cooling water stored in the water tank;
a pump configured to transfer the cooling water and control a speed of the cooling water being transferred,
a radiator disposed between the pump and the transferring member in the temperature adjusting part case;
a heat conductive fixing member capable of transferring heat energy provided between the housing of the second nozzle and the first Peltier member and between the housing of the second nozzle and the first heating member; and
conductive plates including a first conductive plate attached to the first Peltier member and the first heating member in an opposite side of the heat conductive fixing member and a second conductive plate attached to the second Peltier member and the second heating member in an opposite side of the printing plate,
wherein the transferring members are connected to the Peltier members, and
wherein the temperature adjusting part controls the temperature of the fluid state biomaterial accommodated in the second nozzle and controls the temperature of the printing plate for hardening the biomaterial discharged from the second nozzle.

2. The 3D bioprinter of claim 1, wherein the controller controls the temperature adjusting part.

3. The 3D bioprinter of claim 2, wherein the controller is provided to independently control the first nozzle and the second nozzle.

4. The 3D bioprinter of claim 3, wherein:
the controller controls the second nozzle to gradationally discharge the fluid state biomaterial; and
the gradational discharge is performed by a step motor connected to the second nozzle.

5. The 3D bioprinter of claim 4, further comprising an insulation cover configured to surround an exterior of the second nozzle and insulate the second nozzle.

6. The 3D bioprinter of claim 1, wherein a purifying member configured to purify the working space is provided in the case.

* * * * *